United States Patent
Garvey et al.

(10) Patent No.: US 10,363,315 B2
(45) Date of Patent: Jul. 30, 2019

(54) COMPOSITION FOR TREATMENT OF A DETACHED RETINA AND METHOD OF PRODUCTION THEREOF

(75) Inventors: Michael Joseph Garvey, Wirral (GB); Rachel Lucinda Williams, Wirral (GB); Michael Day, Wirral (GB)

(73) Assignee: University of Liverpool, Liverpool, Merseyside (GB)

( * ) Notice: Subject to any disclaimer, the term of this patent is extended or adjusted under 35 U.S.C. 154(b) by 966 days.

(21) Appl. No.: 11/920,584

(22) PCT Filed: May 18, 2006

(86) PCT No.: PCT/EP2006/062432
§ 371 (c)(1),
(2), (4) Date: Nov. 16, 2007

(87) PCT Pub. No.: WO2006/122973
PCT Pub. Date: Nov. 23, 2006

(65) Prior Publication Data
US 2009/0170811 A1    Jul. 2, 2009

(30) Foreign Application Priority Data

May 19, 2005   (GB) .................................. 0510196.9

(51) Int. Cl.
*A61K 47/34* (2017.01)
*A61K 9/00* (2006.01)

(52) U.S. Cl.
CPC ............ *A61K 47/34* (2013.01); *A61K 9/0048* (2013.01)

(58) Field of Classification Search
CPC ............................. A61K 47/34; A61K 9/0048
USPC .................................................... 514/63, 759
See application file for complete search history.

(56) References Cited

U.S. PATENT DOCUMENTS

| 4,879,331 A | 11/1989 | Endo et al. |
| 5,391,590 A | 2/1995 | Gerace et al. |
| 6,547,714 B1 | 4/2003 | Dailey |

FOREIGN PATENT DOCUMENTS

CA        1100931 A   *   5/1981

OTHER PUBLICATIONS

ISR for PCT/EP2006/062432.
Herbert et al. 2004 Gràefe's Arch. Clin. Exp. Opthalmol. 242: 250-254.
Sparrow et al. 1992 RETINA 12: 134-140.
Wetterqvist et al. 2004 Br. J. Opthalmol. 88: 692-696.

* cited by examiner

*Primary Examiner* — Sahar Javanmard
(74) *Attorney, Agent, or Firm* — Sonia K. Guterman; Preeti T. Arun; Lawson & Weitzen LLP

(57) ABSTRACT

The present invention relates to a composition for use in the treatment of a detached retina, comprising an oil and an additive capable of increasing the extensional viscosity of the oil. The present invention also relates to a method and kit of parts for producing the composition.

7 Claims, No Drawings

COMPOSITION FOR TREATMENT OF A DETACHED RETINA AND METHOD OF PRODUCTION THEREOF

CROSS-REFERENCE TO RELATED APPLICATIONS

This application claims the benefit of PCT application serial number PCT/EP2006/062432, filed May 18, 2006, which claims the benefit of Great Britain patent application number GB 050196.9, filed May 19, 2005, the contents of each of which are incorporated herein by reference in their entireties.

The present invention relates to a composition for use in the treatment of retinal detachment. In particular, the composition comprises an oil and an additive capable of increasing the extensional viscosity of the oil.

Retinal detachment is the separation of the neurosensory retina from its underlying pigment epithelium. Untreated, retinal detachment can result in permanent vision loss or blindness. Retinal detachment is caused by traction of the vitreous upon the retina. The traction can be 'dynamic', caused by eye movements and thus relative movement of the vitreous and the retina; or 'static', due to contraction of membranes on the surface of the retina. Retinal detachments are associated with myopia, pseudophakia, trauma and diabetes; it is often the common pathway leading to blindness in a host of ophthalmic eye diseases.

Where a retinal detachment is associated with retinal breaks (also referred to as perforations, holes or tears), fluid gains access from the vitreous cavity to the subretinal space. This form of retinal detachment is referred to as 'Rhegmatogenous'. There are only two effective means of closing retinal breaks. The first involves the application of explants outside the eye in order to buckle the sclera (such as described in U.S. Pat. No. 6,547,714). The second involves the use of internal tamponades. Internal tamponades are agents injected into the vitreous cavity to occlude retinal breaks. They are fluids that are immiscible with water and form an interface with it. The fluid can be gaseous such as air, sulphur hexafluoride ($SF_6$) or perfluoropropane ($C_3F_8$). These gases can be used undiluted in small volumes or mixed with air and totally fill the vitreous cavity. The liquids include perfluorocarbon liquids, semifluorinated alkanes or alkenes and silicone oil. Of these, only silicone oil can be tolerated in the eye for more than a few weeks. Prolonged use of any of the other liquids will give rise to retinal toxicity as demonstrated by inflammatory reaction or by histological changes.

Whilst these methods of treatment can be successful, they often require multiple treatments and there is always a danger of physical damage to the retina itself. Furthermore, there are also other dangers associated with these procedures such as the risk of infection, bleeding, high pressure inside the eye and the possibility of cataract development and these procedures often require a second operation to be undertaken.

Retinal detachments can also be treated by means of pneumatic retinopexy, whereby a gas bubble is injected into the vitreous space so as to help push the retinal tear back against the wall of the eye. This method can also be used in conjunction with the laser and cryo-surgical techniques if required. The gases preferred for such operations are commonly either perfluoropropane ($C_3F_8$) or sulphur hexafluoride ($SF_6$), which when mixed with sterile air have the properties of remaining in the eye for extended periods of time. RU2235527 discloses a number of other gases that may also be used in conjunction with this technique.

Eventually, the gas is replaced by the eyes own natural fluid, although there have been recent concerns over the toxicology of compositions that are fluorine based.

Another method of treatment involves a vitrectomy whereby all or part of the vitreous gel is removed from the eye and replaced with a tamponade agent, such as a perfluorocarbon liquid, silicone oil or a gas (using a similar gaseous composition as described above) and the eye is allowed to fill with the body's own fluid over time. In this technique, a small incision is made in the wall of the eye and the vitreous gel is removed by means of a small cutting device. As the vitreous gel is removed, a saline solution is used to maintain the pressure by a continuous infusion. This solution is then exchanged with an air infusion following which an air and gas mixture is injected. Alternatively, perfluorocarbon liquids, semifluorinated alkanes or alkenes and more commonly silicone oil is injected as a tamponade agent. The tamponade agent is the immiscible fluid that occludes retinal breaks because of its interfacial tension and its buoyancy. The tamponade material is therefore intended to close the retinal tear and reoppose the retina on the underlying choroids.

For a number of years, 1,000 mPas silicone oil has been used clinically as a tamponade agent, but after a period of time within the eye the oil has a tendency to emulsify. The emulsification causes a number of specific problems; firstly the emulsified droplets can stimulate adverse biological responses including inflammatory reactions. Secondly, blocking of fluid to the eye decreases aqueous outflow and can cause raised intraocular pressure and glaucoma. Thirdly, reduction of vision by opacification of the fluid within the eye, and lastly the emulsion cannot tamponade the retina. To reduce the risk of emulsification, 5,000 mPas silicone oil is favoured by a number of clinicians.

The tendency to emulsify is increased by the presence of low molecular weight component silicone oil molecules. Impurities such as cyclical forms of siloxanes also contribute to the tendency of the silicone to disperse. The lower the overall molecular weight of the silicone oil, the lower the viscosity and the less shear force is required to disperse the silicone. Previous attempts to reduce the tendency to dispersion include the manufacture of the so-called highly purified silicone oil, concentrating on removal of the low molecular weight components. Some manufacturers claim to aim for a single molecular weight silicone oil. Others approach the problem by increasing the viscosity and the purity of the medical product, such that 5,000 mPas oil has found favour amongst many surgeons.

However, the high shear viscosity of this oil significantly increases the difficulty of injecting the tamponade agent into the eye and of its subsequent removal from the eye. Whilst highly viscous oils can be injected under increasingly high pressures through small incisions into the eye, the same cannot be said of removal. The maximum suction force that can be generated by a suction pump is one atmosphere pressure, and this often results in a very low flow and thus a long time for the extraction of silicone oil. This often requires a compromise involving the use of a larger bore instrument and cannula which in turn requires the use of larger incisions into the eye. Such large incisions are undesirable surgically. They weaken the eye and increase the chances of collateral damage such as vitreous incarceration or entry site related tears. Hypotony can also follow once the oil has been removed as the balanced salt solution can now flow out relatively unimpeded via an enlarged incision. In all instances it is preferable to have small incisions with the minimal amount of invasive surgery.

It is an object of the present invention to address one or more problems associated with the prior art procedures and in particular to provide a tamponade agent that can be effectively used in the treatment of retinal detachment. Furthermore, it is an object of the present invention to provide a tamponade agent that resists emulsification or substantially prevents emulsification from occurring. It is also an object of the present invention to provide a fluid tamponade agent that is user friendly, with a relatively low shear viscosity.

In accordance with the present invention, there is provided a composition for use in the treatment of a detached retina, comprising an oil and an additive capable of increasing the extensional viscosity of the oil. The composition therefore provides for an oil which can be used to replace part or all of the vitreous gel in the posterior part of the eye, and does not have a propensity to form an emulsion. Thus, the additive can be added to oils (such as those derived from silicone) with viscosities lower than or similar to that commonly used clinically at present. The resultant solution will have a relatively low shear viscosity (when compared to a 5000 mPas silicone oil for example) and have a greater resistance to emulsification due to increased extensional viscosity.

Extensional viscosity can be understood by considering a dilute solution of a high molecular weight linear polymer, where the properties of the solution are governed by the isolated individual polymer coils. At low rates of extension of the solution, the polymer chains are in a loosely spherical configuration and the extensional viscosity is low. At higher extension rates, however, the polymer chains unwind and elongate in line with the direction of extension, presenting a resistance to the applied extensional flow. At a critical extensional flow rate, the polymer chains unwind into a long stretched string. This is known as the coil-stretch transition and results in a large increase in resistance to the applied extension and hence an extensional viscosity that can be many times higher than the equivalent viscosity in shear flow.

The process of emulsification can be considered as the oscillation of shearing of an oil/water interface under an external force which leads to the pulling out of filaments of one liquid into another. These filaments subsequently thin on extension then snap resulting in the formation of satellite droplets that, subject to suitable emulsification stabilisers being present, will persist in the continuous phase. By increasing the extensional viscosity of the oil phase, filament breakage is inhibited and therefore this increase in extensional viscosity hinders satellite droplet formation.

The oil may be a low viscosity oil and an oil that is currently used in procedures for the treatment of retinal detachment. The oil may have a viscosity of less than 5,000 mPas. Preferably, the viscosity of the oil is up to 3,000 mPas. More preferably, the oil has a viscosity of up to 2,000 mPas. Most preferably, the oil has a viscosity of 1,000 mPas.

The oil used in accordance with the present invention may be one which is currently used during the treatment of retinal detachment. It will be evident to the skilled addressee that the term "oil" will also encompass oils which have yet to be developed. Preferably, the oil is selected from one or more of the following: a silicone oil, a perfluorocarbon oil or a semi-fluorinated alkane oil. The oil may also comprise a commercially available perfluorocarbon oil, such as the one marketed by Fluoron GmbH (Germany) under the Densiron® mark.

Preferably, the additive will have a high molecular weight and will be soluble/miscible with the oil. More preferably, the additive will be soluble/miscible with a silicone oil, a perfluorocarbon oil or a semi-fluorinated alkane oil or a mixture thereof. It will be apparent that a number of additives may be suitable for increasing the extensional viscosity of the oil. Additives that will not impair the optical characteristics of the oil will be most desirable. Furthermore, the high molecular weight additives will preferably be those miscible with or soluble in silicone tamponade oils.

The molecular weight of the additive may be greater than 45,000. It is preferred that the molecular weight of the additive is greater than 49,000. Preferably, the molecular weight of the additive will be in the range of 45,000 to 1,500,000.

The additive may also be a polymer and will preferably be a grease or an oil, such as a silicone oil. Other oils may also be used, such as modified oils. Additionally, co-solvents may also be provided with the oil if appropriate/required.

If an oil is used as the additive, it is preferred that such an oil has a viscosity of at least 5,000 mPas. Preferably, the viscosity of the oil is in the range of 10,000-25,000,000 mPas, more preferably in the range of 30,000-20,000,000 mPas, and yet more preferably in the range of 50,000-5,000,000 mPas.

The additive may be a mixture of two or more compounds if required. For example, the additive may be a mixture of two high viscosity silicone oils, such as those having viscosities of 10,000 and 2,500,000 mPas.

It will be apparent to one skilled in the art that the quantity of the additive relative to the quantity of oil will be dependent upon a number of factors, not least the particular molecular weights and/or viscosities of the additive and the oil. For example, a small quantity of a larger molecular weight additive may produce the same increase in extensional viscosity of the silicone oil as a larger quantity of a smaller molecular weight additive. It is preferable that the quantity of additive is relatively low in the composition so that the additive does not detrimentally affect the shear viscosity of the oil. Controlling the shear viscosity of the oil is important so that the composition can be inserted into the eye using the smallest incision as possible. Preferably, the additive is present in a quantity in the range of 0.05-20% w/w of the composition. More preferably, the additive is present in a quantity in the range of 0.05-10% w/w. Even more preferably, the additive is present in a quantity in the range of 0.1-5% w/w of the composition.

In accordance with another aspect of the present invention, there is provided a method of producing a composition for use in the treatment of a detached retina, comprising mixing an oil with an additive capable of increasing the extensional viscosity of the oil. The method may be used to produce a composition as herein above described.

A yet further aspect of the present invention provides for a kit of parts for producing a composition for use in the treatment of a detached retina comprising an oil and an additive capable of increasing the extensional viscosity of the oil. The kit of parts may be used to produce a composition as herein above described.

The kit of parts may further comprise a means by which to contact the oil and the additive together so as to form a mixture prior to use. The kit may therefore provide an apparatus such as a mixing vessel (or similar), so that the composition can be prepared prior to use. The kit may further comprise a means by which to measure a given amount of the oil and the additive prior to mixing and this will allow an individual to prepare a composition with a bespoke extensional viscosity prior to use. Such a kit would also allow a number of different additives to be used in conjunction with the low viscosity silicone oil.

In accordance with yet a further aspect of the present invention, there is provided a composition for use in the treatment of a detached retina, comprising a mixture of a low viscosity silicone oil and a high viscosity silicone oil capable of increasing the extensional viscosity of the low viscosity silicone oil.

Preferably, the viscosity of the low viscosity silicone oil is less than 5,000 mPas and the viscosity of the high viscosity silicone oil is in the range of 5,000-25,000,000 mPas, wherein the high viscosity silicone oil is present in a quantity in the range of 0.05-20% w/w of the composition.

The present invention will now be more particularly described by way of example only with reference to the following examples:

EXAMPLE 1

An experiment was conducted to determine a suitable methodology for assessing the in vitro formation of emulsions in silicone oils. The methodology was then used to undertake proof of principle studies to assess the effect of adding a higher molecular weight silicone oil into lower molecular weight silicone oil.

To simulate the process of emulsification in silicone oils, oils with different viscosity were treated with Pluronic 68, a block copolymer of ethylene oxide and propylene oxide ex BASF, (4% solution) as an emulsification agent. Simultaneously, they were shaken for 3 hours (560 rpm). The emulsification behaviour was analysed and the results are listed in Table 1 below:

TABLE 1

Silicone oils without additive

| Si-Oils (viscosity in mPas) | Emulsification |
|---|---|
| Siol 3 | Yes |
| Siol 1,000 | |
| Siol 5,000 | None |
| Siol 12,500 | |
| Siol 60,000 | |
| Siol 100,000 | |

The results in Table 1 clearly show that silicone oils with a low shear viscosity (of 3 and 1,000 mPas respectively) resulted in emulsification after agitation (intended to simulate the shear forces experienced within the eye). However, silicone oils having a greater shear viscosity (between 5,000-100,000 mPas) did not result in emulsification after agitation. Therefore the methodology as highlighted above would be suitable for simulating the conditions found within a human eye as similar results had been found in the prior art (Siol 5,000 is the favoured vitreous gel replacement).

An experiment was then conducted to assess the emulsification of admixtures of silicone oils of varying shear viscosities, by the addition of a higher viscosity silicone oil to a Siol 1,000 oil. Table 2 below shows the results that were obtained in the experiment:

TABLE 2

Admixtures of silicone oils

| Mixture of Silicone Oils used | Viscosity of Admixture (mPas) | Emulsification | Comment |
|---|---|---|---|
| Siol 1,000 | 1,000 | Yes | Emulsification when viscosity <3,000 mPas |
| Siol 1,000 + Siol 5,000 | 2,000 | | |
| Siol 1,000 + Siol 5,000 | 3,000 | None | |
| Siol 1,000 + Siol 5,000 | 4,000 | | |
| Siol 5,000 | 5,000 | | |

The results in Table 2 clearly show that an admixture of silicone oils having a viscosity of 3,000 mPas or above prevents emulsification.

A further experiment was conducted to assess the use of a small quantity of high molecular weight silicone oil (HMWS) to increase the extensional viscosity of a low molecular weight silicone oil, whilst maintaining a relatively low shear viscosity. The results of the experiment are shown in Table 3 below.

TABLE 3

Silicone oil 1,000 HMWS added

| Silicone Oil | Viscosity (mPas, 25° C.) | Emulsification | Comment |
|---|---|---|---|
| Siol 1,000 (pure) | 963 | Yes | Significant reduction of emulsification in Si-oil 1,030 and 1,300 when adding small amounts of HMWS 100,000 |
| Siol 1,000 + 1% Siol 100,000 | 1030 | None | |
| Siol 1,000 + 5% Siol 100,000 | 1300 | None | |

The results of these experiments illustrated that there was no significant emulsification in silicone oils with a shear viscosity higher than 3,000 mPas. Additionally, significant emulsification was seen in silicone oils with a viscosity lower than 2,000 mPas, but almost no emulsification was seen in silicone oils with a viscosity of 1,030 and 1,300 mPas after the addition of a small amount of a high molecular weight silicone oil (Siol 100,000).

EXAMPLE 2

Experiments were then conducted to assess the shear and extensional viscosities of compositions based upon mixtures of a 1,000 mPas silicone oil and high molecular weight additives and determine whether or not the compositions inhibited emulsification. Pluronic F68 or a protein emulsifier were used as emulsification agents. Distilled water was also used as a control in place of an emulsification agent.

The silicone oil 1000/high molecular weight silicone additive blends were prepared as follows. The silicone oil was added to a polystyrene container (ex Bibby Sterilin) followed by the additive. The mixture was stirred using a roller mixer (model SRT2 ex Stuart Scientific) for 72 hours at ambient temperature and then vigorously mixed for 24 hours using an overhead stirrer (48 hours in the case of the blend containing the 780,000 MW molecular weight silicone additive).

Samples were prepared in 5 ml round bottom long neck quickfit flasks as follows. 0.8 g of water or emulsifier (Pluronic F68 or protein solution) was added to the flask followed by ca. 7 g of oil or oil/additive blend (sufficient to fill the flask to within ca. 0.5 cm of the top of the neck). The flask was allowed to stand for 24 hours at ambient temperature (to purge air bubbles) and then carefully sealed with a dedicated glass stopper to leave the flask full of liquid (i.e. without a liquid-air interface).

For all experiments, Silicone Oil 1000 ex Fluoron (Germany) was used. The high molecular weight silicone additives used were as follows: MW 116,500-PS047.5 ex Fluorochem (England); MW 308,000-PS049.5 ex Fluorochem; MW 423,000-PS050 ex Fluorochem; MW 780,000-Silicone Putty ex NEWI (North Wales).

A 4% solution of Pluronic F68 (ex BASF), or a 0.5% w/w solution of lypholised bovine albumin protein (ex Sigma) in P-4417 phosphate buffered saline (ex Sigma) were used as separate emulsification agents in experiments run in parallel. Distilled water was used in similar experiments as a control and in place of an emulsification agent.

Samples were mixed using a Heidolph Multi REAX mixer. Samples were initially mixed at 250 rpm for 1 hour and then visually assessed immediately and after standing for 1 hour at ambient temperature. Samples showing droplet formation/emulsification were allowed to stand for 24 hours at ambient temperature in order to examine droplet stability. This procedure was repeated at increased mixing speeds of 500, 1000, 1500 and 2000 rpm. Results are provided below for the first agitation speed at which droplet formation/emulsification was observed. The state of the samples immediately after mixing at the specified speed is also provided in the tables below.

Shear viscosities were measured at 25° C. using a TA Instruments Advanced Rheometer AR500. Extensional viscosities were measured at 25° C. using a Haake Caber 1 Extensional Rheometer.

The results for the experiment conducted with water in place of an emulsification agent are shown below in Table 4.

TABLE 4

| System | Shear Viscosity of Oil/Blend (10 s − 1; mPas) | Extensional Viscosity of Oil/Blend (mPas) | State |
|---|---|---|---|
| Silicone Oil 1000/ water | 994 | 3437 | Considerable adhesion of globules to flask surface at 500 rpm Considerable droplet formation at 1000 rpm |
| Silicone Oil 1000 plus 5% 116,500 MW additive/ water | 1311 | 4400 | No droplet formation at 2000 rpm |
| Silicone Oil 1000 plus 5% 308,000 MW additive/ water | 1858 | 6000 | No droplet formation at 2000 rpm |
| Silicone Oil 1000 plus 5% 423,000 MW additive/ water | 2244 | 6700 | No droplet formation at 2000 rpm |

The results for the experiment conducted with Pluronic F68 used as an emulsification agent are shown below in Table 5.

TABLE 5

| System | Shear Viscosity of Oil/Blend (10 s − 1; mPas) | Extensional Viscosity of Oil/Blend (mPas) | State |
|---|---|---|---|
| Silicone Oil 1000/ Pluronic F68 | 994 | 3437 | Moderate droplet formation at 2000 rpm |
| Silicone Oil 1000 plus 1% 116,500 MW/Pluronic F68 | 1128 | 3775 | No droplet formation at 2000 rpm |
| Silicone Oil 1000 plus 5% 308,000 MW additive/ Pluronic F68 | 1858 | 6000 | No droplet formation at 2000 rpm |
| Silicone Oil 1000 plus 5% 423,000 MW additive/ Pluronic F68 | 2244 | 6700 | No droplet formation at 2000 rpm |

The results for the experiment conducted with a protein emulsifier as the emulsification agent are shown below in Table 6.

TABLE 6

| System | Shear Viscosity of Oil/Blend (10 s − 1; mPas) | Extensional Viscosity of Oil/Blend (mPas) | State |
|---|---|---|---|
| Silicone Oil 1000/ Protein | 994 | 3437 | Moderate droplet formation at 2000 rpm |
| Silicone Oil 1000 plus 5% 308,000 MW additive/ Protein | 1858 | 6000 | No droplet formation at 2000 rpm |
| Silicone Oil 1000 plus 5% 423,000 MW additive/ Protein | 2269 | 6950 | No droplet formation at 2000 rpm |
| Silicone Oil 1000 plus 5% 780,000 MW additive/ Protein | 4320 | 12200 | No droplet formation at 2000 rpm |

It is evident that addition of the high molecular weight silicone additive has significantly increased the resistance of the Silicone Oil 1000 to droplet formation/emulsification.

These experiments show that use of a high molecular weight additive is capable of increasing the extensional viscosity of a silicone oil having a relatively low viscosity (1000 mPas). The additive prevents emulsification of the silicone oil in vitro. It is highly likely that using a mixture of a low viscosity oil (such as silicone oil) and an additive which increases the extensional viscosity of the oil will also perform a similar function in vivo and will be suitable for the treatment of a detached retina.

The invention claimed is:

1. A composition for medical use in treatment of a detached retina, the composition comprising an oil and an additive capable of increasing the extensional viscosity of the oil, wherein the oil has a viscosity of less than 5,000 mPas and is at least one selected from the group consisting of: a silicone oil, a perfluorocarbon oil, and a semi-fluorinated alkane oil, wherein the additive is a silicone oil having a viscosity of 2,500,000 mPas, and is present in the range of 0.05%-20% w/w of the composition, the composition effective to prevent formation of an emulsion with protein, for the medical use of the composition in the treatment of the detached retina.

2. A composition as claimed in claim 1, wherein the oil has a viscosity of up to 3,000 mPas.

3. A composition as claimed in claim 1, wherein the additive is oil soluble/miscible.

4. A composition as claimed in claim 1, wherein the additive is present in a quantity in the range of 0.1-5% w/w of the composition.

5. A composition as claimed in claim 1, wherein the additive is present in the range of 0.1%-10% w/w of the composition.

6. A composition as claimed in claim 1, wherein the additive has a molecular weight greater than 10,000.

7. A composition as claimed in claim 1, wherein the additive has a molecular weight greater than 45,000.

* * * * *